US000001996B1

(19) United States

(12) Statutory Invention Registration

Peake et al.

(10) Reg. No.: US H1996 H

(43) Published: Oct. 2, 2001

(54) INSECTICIDAL PHOTOSTABLE ACID SALT DERIVATIVES OF N-BENZYL-4-BENZHYDROLPIPERIDINES

(75) Inventors: Clinton J. Peake, Trenton; Thomas G. Cullen, Milltown; Robert N. Henrie, II, Pennington; Jane A. Dybas, Flemington, all of NJ (US)

(73) Assignee: FMC Corporation, Philadelphia, PA (US)

(21) Appl. No.: 09/196,880

(22) Filed: Nov. 20, 1998

Related U.S. Application Data

(60) Provisional application No. 60/067,072, filed on Nov. 20, 1997.

(51) Int. Cl.[7] ..... C07D 421/00; C07D 211/08; C07D 211/68; C07D 401/00

(52) U.S. Cl. ..... 546/199; 546/192; 546/194; 546/210; 514/317; 514/318; 514/326

(58) Field of Search ..... 546/192, 194, 546/210; 514/317, 318, 326

(56) References Cited

U.S. PATENT DOCUMENTS

| | | | | |
|---|---|---|---|---|
| 5,077,301 | | 12/1991 | Pein et al. . | |
| 5,569,664 | * | 10/1996 | Silverman et al. | 514/317 |
| 5,639,763 | * | 6/1997 | Silverman et al. | 514/321 |
| 5,795,901 | * | 8/1998 | Szcepanski | 514/326 |

FOREIGN PATENT DOCUMENTS

| | | |
|---|---|---|
| WO 96/36228 | 11/1996 | (WO) . |
| WO 97/22583 | 6/1997 | (WO) . |

* cited by examiner

*Primary Examiner*—Patricia Morris
*Assistant Examiner*—Aileen J. Baker
(74) *Attorney, Agent, or Firm*—Paul A. Fair; James D. Goodell; John Sheehan

(57) ABSTRACT

It has now been found that certain novel photostable agriculturally acceptable organic or inorganic salts of formula I are useful as insecticides:

I

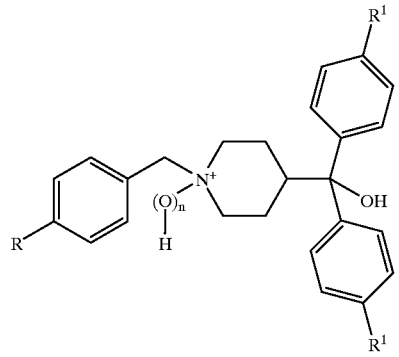

where

R is alkoxycarbonyl, alkoxycarbonylamino, cycloalkylalkoxy, 2-alkyl-2H-tetrazol-5-yl, or 2-haloalkyl-2H-tetrazol-5-yl; $R^1$ is trihaloalkyl, or trihaloalkoxy; n is 0, or 1; and, wherein said salts are derived from hydrochloric acid; hydrobromic acid; boric acid; phosphoric acid; maleic acid; fumaric acid; phthalic acid; salicylic acid optionally substituted with alkyl or halogen; D-glucuronic acid; the sulfonic acid $R^2SO_3H$ where $R^2$ is alkyl, haloalkyl, hydroxyalkyl, D-10-camphoryl, or phenyl optionally substituted with alkyl or halogen; the carboxylic acid $R^3CO_2H$ where $R^3$ is hydrogen, alkyl, trihaloalkyl, carboxyl, phenyl optionally substituted with alkyl or halogen, or pyridyl; the boronic acid $R^4B(OH)_2$ where $R^4$ is alkyl or phenyl optionally substituted with alkyl or halogen; the phosphonic acid $R^5PO_3H_2$ where $R^5$ is alkyl, haloalkenyl, or phenyl optionally substituted with alkyl or halogen; the sulfuric acid $R^6OSO_3H$ where $R^6$ is hydrogen or alkyl; or the alkanoic acid $X\text{-}(CH_2)_qCO_2H$ where q is 0 to 11, X is halogen, trihaloalkyl, haloalkenyl, cyano, aminocarbonyl, or $CO_2R^7$ where $R^7$ is hydrogen or alkyl. Preferred compounds include those where R is 2-ethyl-2H-tetrazol-5-yl; $R^1$ is trifluoromethyl; n is 1; and said salts are derived from hydrochloric acid, or the sulfonic acid $R^2SO_3H$ where $R^2$ is alkyl, or hydroxyalkyl.

18 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

INSECTICIDAL PHOTOSTABLE ACID SALT DERIVATIVES OF N-BENZYL-4-BENZHYDROLPIPERIDINES

This application derives priority from verified provisional application No. 60/067,072 filed Nov. 20, 1997, now abandoned.

BACKGROUND OF THE INVENTION

This invention relates generally to insecticidal compounds for use in controlling insects. In particular, it pertains to certain agriculturally acceptable organic and inorganic acid salt derivatives of N-benzyl-4-benzhydrolpiperidines and their corresponding N-oxides having improved photostability while providing insecticidal activity generally equivalent to the parent compound. This invention also pertains to the insecticidal compositions of these salt derivatives, and a method of controlling insects at a locus which comprises applying to that locus a compound of the invention or an insecticidal composition containing the compound.

There is a continuing demand for new insecticides that are safer, more effective, and less costly. Insecticides are useful for controlling insects which may otherwise cause significant damage to crops such as wheat, corn, soybeans, potatoes, and cotton to name a few. For crop protection, insecticides are desired which can control the insect pests without damaging the crops, and which have no deleterious effects to mammals and other living organisms. Photostable insecticides are advantageous in that they promote residual insecticidal activity which increases the effectiveness of the insecticidally active material.

U.S. Pat. No. 5,569,664 and U.S. Pat. No. 5,639,763 disclose a class of piperidine derivatives, the corresponding N-oxides and agriculturally acceptable salts for use as insecticides:

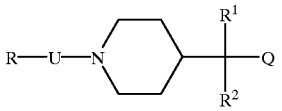

in which, among others,

U is —$(CH_2)_n$— where n is 1, 2, or 3;

Q is hydroxy;

R is selected from a heterocycle having 5 or 6 ring atoms, optionally fused to a benzene ring, and

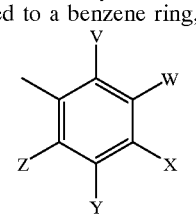

where

V, W, Y, and Z are hydrogen; and,

X is hydrogen, hydroxy, halogen, alkyl, alkoxyalkyl, alkoxy, cycloalkylalkoxy, haloalkoxy, alkenyloxy, haloalkenyloxy, alkynyloxy, alkylsilyloxy, alkylthio, haloalkylthio, cyano, cyanoalkoxy, nitro, amino, monoalkylamino, dialkylamino, alkylaminoalkoxy, alkylcarbonylamino, alkylcarbonyl, alkoxycarbonylamino, alkoxycarbonyl, alkylaminocarbonyl, aminocarbonyloxy, phenyl, phenylalkoxy, phenoxy, phenoxyalkyl, or a five- or six-membered heterocycl; each cycloalkyl moiety, heterocycle, or phenyl ring is optionally substituted with halogen, alkoxy, or haloalkoxy;

W and X taken together may be —$OCH_2CH_2O$—, —$CH_2C(CH_3)_2O$—, —$OC(CH_3)_2O$—, —N=C$(C_2H_5)$O—, or —CH=CHCH=C—;

$R^1$ and $R^2$ are independently selected from phenyl substituted with one or more haloalkyl or haloalkoxy.

The '664 and '763 patents do not disclose improved photostablility of agriculturally acceptable salts of piperidines or piperidine N-oxides.

SUMMARY OF THE INVENTION

It has now been found that certain novel agriculturally acceptable organic and inorganic acid salts of N-benzyl-4-benzhydrolpiperidines and their corresponding N-oxides have improved photostablility, and are useful as insecticides. These compounds are represented by formula I:

I

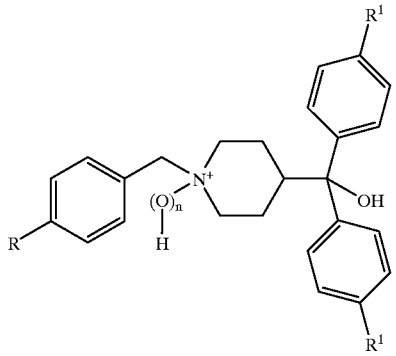

wherein R, $R^1$, and n are as defined below. Preferred compounds include those where R is 2-alkyl-2H-tetrazol-5-yl; $R^1$ is trifluoromethyl, or trifluoromethoxy; n is 1; and said salts are derived from hydrochloric acid, or a sulfonic acid.

DETAILED DESCRIPTION OF THE INVENTION

Certain novel photostable agriculturally acceptable organic and inorganic acid salts of N-benzyl-4-benzhydrolpiperidines and their corresponding N-oxides are useful in controlling insects. These compounds are represented by formula I:

I

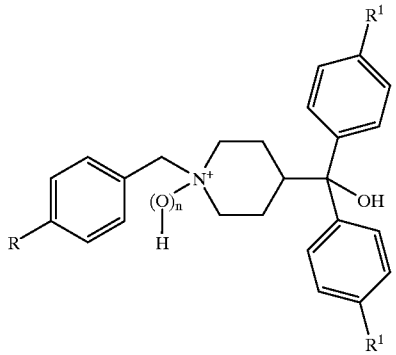

where

R is alkoxycarbonyl, alkoxycarbonylamino, cycloalkylalkoxy, 2-alkyl-2H-tetrazol-5-yl, or 2-haloalkyl-2H-tetrazol-5-yl;

$R^1$ is trihaloalkyl, or trihaloalkoxy;

n is 0, or 1; and, wherein said salts are derived from hydrochloric acid; hydrobromic acid; boric acid; phosphoric acid, maleic acid, fumaric acid, phthalic acid; salicylic acid optionally substituted with alkyl or halogen; D-glucuronic acid; the sulfonic acid $R^2SO_3H$ where $R^2$ is alkyl, haloalkyl, hydroxyalkyl, D-10-camphoryl, or phenyl optionally substituted with alkyl or halogen; the carboxylic acid $R^3CO_2H$ where $R^3$ is hydrogen, alkyl, trihaloalkyl, carboxyl, phenyl optionally substituted with alkyl or halogen, or pyridyl; the boronic acid $R^4B(OH)_2$ where $R^4$ is alkyl or phenyl optionally substituted with alkyl or halogen; the phosphonic acid $R^5PO_3H_2$ where $R^5$ is alkyl, haloalkenyl, or phenyl optionally substituted with alkyl or halogen; the sulfuric acid $R^6OSO_3H$ where $R^6$ is hydrogen or alkyl; or the alkanoic acid $X\text{-}(CH_2)_qCO_2H$ where q is 0 to 11, X is halogen, trihaloalkyl, haloalkenyl, cyano, aminocarbonyl, or $CO_2R^7$where $R^7$ is hydrogen or alkyl.

Preferred compounds are those where R is alkoxycarbonyl, alkoxycarbonylamino, cycloalkylalkoxy, 2-alkyl-2H-tetrazol-5-yl, or 2-haloalkyl-2H-tetrazol-5-yl; $R^1$ is trihaloalkyl, or trihaloalkoxy; n is 0, or 1; and, wherein said salts are derived from hydrochloric acid, salicylic acid optionally substituted with alkyl or halogen, D-glucuronic acid, or the sulfonic acid $R^2SO_3H$ where $R^2$ is alkyl, haloalkyl, hydroxyalkyl, D-10-camphoryl, or phenyl optionally substituted with alkyl or halogen.

Particularly preferred compounds are those where R is 2-ethyl-2H-tetrazol-5-yl; $R^1$ is trifluoromethyl; n is 1; and said salts are derived from hydrochloric acid, or the sulfonic acid $R^2SO_3H$ where $R^2$ is alkyl, or hydroxyalkyl.

As used in this specification and unless otherwise indicated the term "alkyl" and "alkoxy" used alone or as part of a larger moiety includes 1 to 6 carbon atoms either straight or branched chain. "Alkenyl" refers to 2 to 12 carbon atoms, preferably 2 to 6 carbon atoms, either straight or branched chain. "Cycloalkyl" refers to 3 to 8 carbon atoms, preferably 3 to 6 carbon atoms. "Halogen" or "Halo" refer to chlorine, bromine, and fluorine. "HPLC" refers to high pressure liquid chromatography, and "DMSO" refers to dimethyl sulfoxide.

The photostable, agriculturally acceptable acid salts of N-benzyl-4-benzhydrolpiperidines and their corresponding N-oxides of formula I may be prepared by methods described below or by methods similar to those known in the art for similar compounds. In general, the parent N-benzyl-4-benzhydrolpiperidines may be prepared as described in U.S. Pat. No. 5,569,664 by reacting a 4-benzhydrolpiperidine with a benzyl halide. This patent also describes a method for oxidizing the N-benzyl-4-benzhydrolpiperidines by treatment with, for example, 50% 3-chloroperoxybenzoic acid in a suitable solvent, to give the corresponding N-benzyl-4-benzhydrolpiperidine N-oxides. The acid salts of formula I may then be obtained by treatment of an appropriately substituted N-benzyl-4-benzhydrolpiperidine in a solvent with an acid, to give the corresponding acid salts of N-benzyl-4-benzhydrolpiperidine I.

A procedure for a method useful to prepare compounds of this invention is given in the example below.

EXAMPLE

Synthesis of N-[4-(2-ethyl-2H-tetrazol-5-yl) phenylmethyl]-4-[bis(4-trifluoro-methylphenyl) hydroxymethyl]piperidine N-oxide ethanesulfonic acid salt (Compound 33)

A suspension of 10.0 grams (0.017 mole) of N-[4-(2-ethyl-2H-tetrazol-5-yl)phenylmethyl]-4-[bis(4-trifluoromethylphenyl)hydroxymethyl]piperidine N-oxide in 10 mL of ethanol was stirred, and 3.0 mL (0.037 mole) of ethanesulfonic acid was added dropwise. Upon completion of addition the reaction mixture was stirred at ambient temperature for about 10 minutes, diluted with 500 mL of diethyl ether, and then stirred for an additional 30 minutes. After this time a white solid was collected by filtration. The solid was washed with diethyl ether and dried at 60 ° C., yielding 10.5 grams of Compound 33, mp 187–193 ° C. The NMR spectrum was consistent with the proposed structure.

| | Elemental Analyses: $C_{32}H_{35}N_2O_5SF_6$ | | | |
|---|---|---|---|---|
| | Carbon | Hydrogen | Nitrogen | Fluorine |
| % Theoretical | 53.70 | 4.93 | 9.79 | 15.93 |
| % Found | 53.46 | 4.83 | 9.68 | 16.20 |

Table 1 below shows representative compounds of the present invention.

TABLE 1

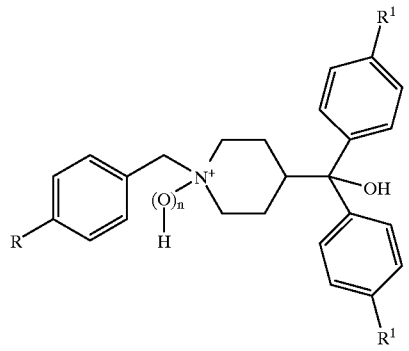

| Cmpd. No. | R | $R^1$ | n | Salt Derived From $R^2SO_3H$ or Other Acid: $R^2$ | Acid |
|---|---|---|---|---|---|
| 1 | $CO_2CH(CH_3)_2$ | $OCF_3$ | 0 | — | HCl |
| 2 | $CO_2CH(CH_3)_2$ | $OCF_3$ | 0 | $C_2H_5$ | — |
| 3 | 2-methyl-2H-tetrazol-5-yl | $CF_3$ | 0 | — | HCl |
| 4 | 2-methyl-2H-tetrazol-5-yl | $OCF_3$ | 0 | — | HCl |

TABLE 1-continued

| | | | | | |
|---|---|---|---|---|---|
| 5 | 2-methyl-2H-tetrazol-5-yl | $OCF_3$ | 0 | $C_2H_5$ | — |
| 6 | 2-ethyl-2H-tetrazol-5-yl | $CF_3$ | 0 | — | HCl |
| 7 | 2-ethyl-2H-tetrazol-5-yl | $CF_3$ | 0 | $C_2H_5$ | — |
| 8 | 2-ethyl-2H-tetrazol-5-yl | $OCF_3$ | 0 | — | HCl |
| 9 | 2-ethyl-2H-tetrazol-5-yl | $OCF_3$ | 0 | $C_2H_5$ | — |
| 10 | 2-(2-fluoroethyl)-2H-tetrazol-5-yl | $OCF_3$ | 0 | — | HCl |
| 11 | cyclopropylmethoxy | $CF_3$ | 1 | — | HCl |
| 12 | cyclopropylmethoxy | $CF_3$ | 1 | $C_2H_5$ | — |
| 13 | cyclopropylmethoxy | $CF_3$ | 1 | $C_2H_4OH$ | — |
| 14 | cyclopropylmethoxy | $CF_3$ | 1 | — | salicylic acid |
| 15 | cyclopropylmethoxy | $CF_3$ | 1 | — | D-glucuronic acid |
| 16 | $NHCO_2CH_3$ | $OCF_3$ | 1 | — | HCl |
| 17 | $NHCO_2CH_3$ | $OCF_3$ | 1 | $C_2H_5$ | — |
| 18 | $NHCO_2CH_3$ | $OCF_3$ | 1 | $C_2H_4OH$ | — |
| 19 | $NHCO_2CH_3$ | $OCF_3$ | 1 | — | salicylic acid |
| 20 | $NHCO_2CH_3$ | $OCF_3$ | 1 | — | D-glucuronic acid |
| 21 | $NHCO_2CH(CH_3)_2$ | $CF_3$ | 1 | — | HCl |
| 22 | $NHCO_2CH(CH_3)_2$ | $CF_3$ | 1 | $C_2H_5$ | — |
| 23 | $NHCO_2CH(CH_3)_2$ | $CF_3$ | 1 | $C_2H_4OH$ | — |
| 24 | $NHCO_2CH(CH_3)_2$ | $CF_3$ | 1 | — | salicylic acid |
| 25 | $NHCO_2CH(CH_3)_2$ | $CF_3$ | 1 | — | D-glucuronic acid |
| 26 | 2-methyl-2H-tetrazol-5-yl | $CF_3$ | 1 | — | HCl |
| 27 | 2-methyl-2H-tetrazol-5-yl | $CF_3$ | 1 | $C_2H_5$ | — |
| 28 | 2-methyl-2H-tetrazol-5-yl | $CF_3$ | 1 | $C_2H_4OH$ | — |
| 29 | 2-methyl-2H-tetrazol-5-yl | $CF_3$ | 1 | — | salicylic acid |
| 30 | 2-methyl-2H-tetrazol-5-yl | $CF_3$ | 1 | — | D-glucuronic acid |
| 31 | 2-ethyl-2H-tetrazol-5-yl | $CF_3$ | 1 | — | HCl |
| 32 | 2-ethyl-2H-tetrazol-5-yl | $CF_3$ | 1 | $CH_3$ | — |
| 33 | 2-ethyl-2H-tetrazol-5-yl | $CF_3$ | 1 | $C_2H_5$ | — |
| 34 | 2-ethyl-2H-tetrazol-5-yl | $CF_3$ | 1 | $C_5H_{11}$ | — |
| 35 | 2-ethyl-2H-tetrazol-5-yl | $CF_3$ | 1 | $C_6H_{13}$ | — |
| 36 | 2-ethyl-2H-tetrazol-5-yl | $CF_3$ | 1 | $CF_3$ | — |
| 37 | 2-ethyl-2H-tetrazol-5-yl | $CF_3$ | 1 | $C_6H_5$ | — |
| 38 | 2-ethyl-2H-tetrazol-5-yl | $CF_3$ | 1 | 4-$(CH_3)C_6H_4$ | — |
| 39 | 2-ethyl-2H-tetrazol-5-yl | $CF_3$ | 1 | 2,4,6-$(CH_3)_3C_6H_2$ | — |
| 40 | 2-ethyl-2H-tetrazol-5-yl | $CF_3$ | 1 | D-10-camphor | — |
| 41 | 2-ethyl-2H-tetrazol-5-yl | $CF_3$ | 1 | $C_2H_4OH$ | — |
| 42 | 2-ethyl-2H-tetrazol-5-yl | $CF_3$ | 1 | — | — |
| 43 | 2-ethyl-2H-tetrazol-5-yl | $CF_3$ | 1 | — | 5-Cl-salicylic acid |
| 44 | 2-ethyl-2H-tetrazol-5-yl | $CF_3$ | 1 | — | D-glucuronic acid |
| 45 | 2-ethyl-2H-tetrazol-5-yl | $CF_3$ | 0 | $CH_3$ | — |
| 46 | 2-ethyl-2H-tetrazol-5-yl | $CF_3$ | 0 | — | HBr |
| 47 | 2-ethyl-2H-tetrazol-5-yl | $CF_3$ | 0 | 4-$(CH_3)C_6H_4$ | — |
| 48 | 2-ethyl-2H-tetrazol-5-yl | $CF_3$ | 0 | — | D-glucuronic acid |
| 49 | 2-ethyl-2H-tetrazol-5-yl | $CF_3$ | 0 | $C_2H_4OH$ | — |
| 50 | 2-ethyl-2H-tetrazol-5-yl | $CF_3$ | 0 | — | salicylic acid |
| 51 | 2-ethyl-2H-tetrazol-5-yl | $CF_3$ | 1 | — | 3-$CH_3$-salicylic acid |
| 52 | 2-ethyl-2H-tetrazol-5-yl | $CF_3$ | 1 | 4-$ClC_6H_4$ | — |
| 53 | 2-ethyl-2H-tetrazol-5-yl | $CF_3$ | 1 | — | $H_3BO_3$ |
| 54 | 2-ethyl-2H-tetrazol-5-yl | $CF_3$ | 1 | — | $H_3PO_4$ |
| 55 | 2-ethyl-2H-tetrazol-5-yl | $CF_3$ | 1 | — | maleic acid |
| 56 | 2-ethyl-2H-tetrazol-5-yl | $CF_3$ | 1 | — | fumaric acid |
| 57 | 2-ethyl-2H-tetrazol-5-yl | $CF_3$ | 1 | — | phthalic acid |

| Cmpd. No. | R | $R^1$ | n | Salt Derived From $R^3CO_2H$ $R^3$ |
|---|---|---|---|---|
| 58 | 2-ethyl-2H-tetrazol-5-yl | $CF_3$ | 1 | H |
| 59 | 2-ethyl-2H-tetrazol-5-yl | $CF_3$ | 1 | $CH_3$ |
| 60 | 2-ethyl-2H-tetrazol-5-yl | $CF_3$ | 1 | $CF_3$ |
| 61 | 2-ethyl-2H-tetrazol-5-yl | $CF_3$ | 1 | $CO_2H$ |
| 62 | 2-ethyl-2H-tetrazol-5-yl | $CF_3$ | 1 | 4-Cl-phenyl |
| 63 | 2-ethyl-2H-tetrazol-5-yl | $CF_3$ | 1 | 4-$CH_3$-phenyl |
| 64 | 2-ethyl-2H-tetrazol-5-yl | $CF_3$ | 1 | pyridin-2-yl |

| Cmpd. No. | R | $R^1$ | n | Salt Derived From $R^4B(OH)_2$ $R^4$ |
|---|---|---|---|---|
| 65 | 2-ethyl-2H-tetrazol-5-yl | $CF_3$ | 1 | $CH_3$ |
| 66 | 2-ethyl-2H-tetrazol-5-yl | $CF_3$ | 1 | 4-Cl-phenyl |
| 67 | 2-ethyl-2H-tetrazol-5-yl | $CF_3$ | 1 | 4-$CH_3$-phenyl |

| Cmpd. No. | R | $R^1$ | n | Salt Derived From $R^5PO_3H_2$ $R^5$ |
|---|---|---|---|---|
| 68 | 2-ethyl-2H-tetrazol-5-yl | $CF_3$ | 1 | $CH_3$ |
| 69 | 2-ethyl-2H-tetrazol-5-yl | $CF_3$ | 1 | 4-Cl-phenyl |

TABLE 1-continued

| | | | | |
|---|---|---|---|---|
| 70 | 2-ethyl-2H-tetrazol-5-yl | $CF_3$ | 1 | 4-$CH_3$-phenyl |
| 71 | 2-ethyl-2H-tetrazol-5-yl | $CF_3$ | 1 | $CH_2CF{=}CF_2$ |

| Cmpd. No. | R | $R^1$ | n | Salt Derived From $R^6OSO_3H$ $R^6$ |
|---|---|---|---|---|
| 72 | 2-ethyl-2H-tetrazol-5-yl | $CF_3$ | 1 | H |
| 73 | 2-ethyl-2H-tetrazol-5-yl | $CF_3$ | 1 | $CH_3$ |

| Cmpd. No. | R | $R^1$ | n | Salt Derived From $X\text{-}(CH_2)_qCO_2H$ q | X |
|---|---|---|---|---|---|
| 74 | 2-ethyl-2H-tetrazol-5-yl | $CF_3$ | 1 | 2 | Cl |
| 75 | 2-ethyl-2H-tetrazol-5-yl | $CF_3$ | 1 | 2 | $CF_3$ |
| 76 | 2-ethyl-2H-tetrazol-5-yl | $CF_3$ | 1 | 1 | $CF{=}CF_2$ |
| 77 | 2-ethyl-2H-tetrazol-5-yl | $CF_3$ | 1 | 1 | CN |
| 78 | 2-ethyl-2H-tetrazol-5-yl | $CF_3$ | 1 | 2 | $CONH_2$ |

| Cmpd. No. | R | $R^1$ | n | Salt Derived From $X\text{-}(CH_2)_qCO_2H$ q | X | $R^7$ |
|---|---|---|---|---|---|---|
| 79 | 2-ethyl-2H-tetrazol-5-yl | $CF_3$ | 1 | 4 | $CO_2R^7$ | H |
| 80 | 2-ethyl-2H-tetrazol-5-yl | $CF_3$ | 1 | 8 | $CO_2R^7$ | $CH_3$ |

TABLE 2

Characterizing Data

| Cmpd No | Melting Point ° C. |
|---|---|
| 1 | SOLID |
| 2 | 123–128 |
| 3 | 178–185 |
| 4 | SOLID |
| 5 | 136–140 |
| 6 | 178–185 |
| 7 | 160–173 |
| 8 | SOLID |
| 9 | 126–130 |
| 10 | 112–116 |
| 11 | 171–175 |
| 16 | 160–165 |
| 31 | 214–216 |
| 33 | 187–193 |
| 45 | 82–85 |
| 47 | 138–140 |
| 50 | 75–77 |

PHOTOSTABILITY TESTING

Compounds of the present invention were subjected to determinations of their photostability in side-by-side tests with their non-ionic parent analogs. These photostability tests are conducted as follows:

For each compound tested, four glass microscope coverslips (12 mm in diameter) for each illumination period (0, 3, 6, 12, 24, 48, and 96 hours) are spotted with 10 microliters of a one mg/mL acetonitrile or methanol solution of test compound. The solutions are allowed to evaporate leaving a thin film of test compound on each coverslip. The four coverslips representing the zero hour illumination period are placed in a 20 mL scintillation vial. In the vile is placed one mL of acetonitrile, which extracts the test chemical from the coverslip. The solution is then transferred to a two dram vile for analysis by HPLC. The average HPLC peak area generated by this sample defines the initial level of test compound. The remaining coverslips are then placed in the water-cooled chamber of the exposure platform of a Suntest CPS illuminator (Heraeus Instruments GmbH; Bereich Original Hanau, Hersaeusstrasse R-14, Postfach 1563, D-6450 Hanau 1). The exposure platform is covered with a quartz plate and maintained at about 25° C. for the duration of the test. The Suntest CPS illuminator employs a filtered xenon lamp, which provides illumination of a similar spectrum and intensity as sunlight. Four coverslips for each test compound are removed from the illuminator at the end of each illumination period described above. The four coverslips from each of the illumination periods are treated as described above and the acetonitrile extract is analyzed by HPLC. The average HPLC peak area from each of the illumination periods represents a diminished amount of test compound when compared to the initial level of test compound as determined from the zero hour illumination sample. The percents of test compound remaining from each of these illumination periods are used to generate a degradation curve from which a half life in hours is determined for each test compound.

Table 3 shows the improved photostability of representative compounds of the present invention when compared to the photostability of their non-ionic amino parent. The test compounds are identified by numbers which correspond to those in Table 1.

Photostability Data

| Compound Number | Half-life (Hrs) |
|---|---|
| 7 | 23.0 |
| A* | 5.5 |
| 33 | 34.0 |
| B* | 13.9 |

*A is the non-ionic amino parent of Cmpd. 7
*B is the non-ionic amino N-oxide parent of Cmpd. 33

Representative compounds of the present invention were shown to be about 2.5 to 4 times more photostable than their non-ionic parents in the tests conducted.

BIOLOGICAL TESTING

Candidate insecticides are evaluated for activity against tobacco budworm (*Heliothis virescens* [Fabricius]) by applications to the surface of a wheat germ-based artificial insect diet. Solutions of the candidate insecticides are prepared for testing by diluting a standard 50 millimolar DMSO solution of each candidate insecticide with DMSO, then further diluting with a 1:1 water/acetone solution (V/V). Forty microliters of this solution of calculated concentration is then pipetted onto the surface of the diet in each of six containers, to provide six replicates for each rate of application. Once treated, the contents of the containers are allowed to dry, leaving the calculated concentration ( in millimoles) of candidate insecticide on the surface of the diet. In each container is placed one second instar tobacco budworm larvea. The container is sealed with a transparent film, and then held in a growth chamber for five days. After the five-day exposure period the insecticidal activity of the candidate insecticide is recorded as percent mortality when compared to the total number of insects infested.

It is expected that all formulations normally employed in applications of insecticides would be usable with the compounds of the present invention. These include wettable powders, emulsifiable concentrates, suspension concentrates, water suspensions, flowable concentrates, and the like.

Insecticidal activity at a concentration of candidate insecticide of 0.0025 millimoles on the surface of the diet is given for various compounds of this invention in Table 4.

Insecticidal Activity of Candidate Insecticide Applied to the Surface of the Diet of Tobacco Budworm

| | Cmpd. No | | | | | | | |
|---|---|---|---|---|---|---|---|---|
| | 1 | 2 | 3 | 4 | 5 | 6 | 7 | 8 |
| Percent Mortality | 100 | 100 | 100 | 100 | 100 | 100 | 100 | 100 |
| | Cmpd. No | | | | | | | |
| | 9 | 10 | 11 | 16 | 31 | 33 | A* | B* |
| Percent Mortality | 100 | 100 | 100 | 100 | 100 | 100 | 100 | |

*A is the non-ionic amino parent of Cmpd. 7
*B is the non-ionic amino N-oxide parent of Cmpd. 33

For insecticidal application, the active compounds are formulated into insecticidal compositions by admixture in insecticidally effective amount with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present insecticidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These insecticidal compositions may be applied either as water-diluted sprays, or dusts, or granules to the areas in which insect control is desired. These formulations may contain as little as 0.1%, 0.2% or 0.5% to as much as 95% or more by weight of active ingredient.

Dusts are free flowing admixtures of the active ingredients with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the insecticidal compound and 99.0 parts of talc.

Wettable powders are in the form of finely divided particles which disperse readily in water or other dispersant. The wettable powder is ultimately applied to the locus where insect control is desired either as a dry dust or as an emulsion in water or other liquid. Typical carriers for wettable powders include Fuller's earth, kaolin clays, silicas, and other highly absorbent, readily wet, inorganic diluents. Wettable powders normally are prepared to contain about 5–80% of active ingredient, depending on the absorbency of the carrier, and usually also contain a small amount of a wetting, dispersing, or emulsifying agent to facilitate dispersion. For example, a useful wettable powder formulation contains 80.8 parts of the insecticidal compound, 17.9 parts of Palmetto clay, and 1.0 part of sodium lignosulfonate and 0.3 part of sulfonated aliphatic polyester as wetting agents.

Other useful formulations for insecticidal applications are emulsifiable concentrates (ECs) which are homogeneous liquid compositions dispersible in water or other dispersant, and may consist entirely of the insecticidal compound and a liquid or solid emulsifying agent, or may also contain a liquid carrier, such as xylene, heavy aromatic naphthas, isophorone, or other non-volatile organic solvent. For insecticidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the insecticidal composition.

Suspension Concentrates (SCs) are similar to ECs except that the active ingredient is suspended in a liquid carrier, generally water. SCs, like ECs, may include a small amount of a surfactant, and contain active ingredient in the range of 0.5 to 95%, frequently from 5 to 50%, by weight of the composition. For application, SCs may be diluted in water or other liquid vehicle, and are normally applied as a spray to the area to be treated.

Typical wetting, dispersing, or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agents, when used, normally comprise from 1 to 15% by weight of the composition.

Other useful formulations include suspensions of the active ingredient in a relatively non-volatile solvent such as corn oil, kerosene, propylene glycol, or other suitable solvents.

Still other useful formulations for insecticidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as carbon dioxide, propane, or butane, may also be used. Water-soluble or water-dispersible granules are also useful formulations for insecticidal application of the present compounds. Such granular formulations are free-flowing, non-dusty, and readily water-soluble or water-miscible. The soluble or dispersible granular formulations described in U.S. Pat. No. 3,920,442 are useful herein with the present insecticidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active insecticidal compounds of this invention may be formulated and/or applied with other insecticides, fungicides, nematicides, plant growth regulators, fertilizers, or other agricultural chemicals. In using an active compound of this invention, whether formulated alone or with other agricultural chemicals, to control insects, an effective amount and concentration of the active compound is applied to the locus where control is desired. The locus may be, e.g., the insects themselves, plants upon which the insects feed, or the insect habitat. When the locus is the soil, e.g., soil in which agricultural crops have been or will be planted, the composition of the active compound may be applied to and optionally incorporated into the soil. For most applications the effective amount may be as low as, e.g. about 10 to 500 g/ha, preferably about 100 to 250 g/ha.

It is apparent that various modifications may be made in the formulation and application of the compounds of this invention without departing from the inventive concepts herein as defined in the claims

We claim:

1. An insecticidal, photostable, agriculturally acceptable acid salt of an organic or inorganic acid having the formula:

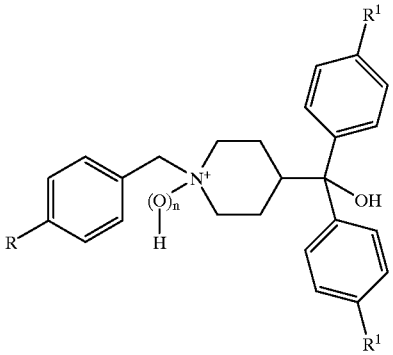

where

R is alkoxycarbonyl, alkoxycarbonylamino, cycloalkylalkoxy, 2-alkyl-2H-tetrazol-5-yl, or 2-haloalkyl-2H-tetrazol-5-yl;

$R^1$ is trihaloalkyl, or trihaloalkoxy;

n is 0,or 1; and, wherein said salt is at least about 2.5 times more photostable than its non-ionic parent and is derived from hydrochloric acid, hydrobromic acid, boric acid, phosphoric acid, maleic acid, fumaric acid, phthalic acid, D-glucuronic acid; the sulfonic acid $R^2SO_3H$ where $R^2$ is alkyl, haloalkyl, hydroxyalkyl, D-10-camphoryl, or phenyl optionally substituted with alkyl or halogen; the carboxylic acid $R^3CO_2H$ where $R^3$ is hydrogen, alkyl, trihaloalkyl, carboxyl, phenyl optionally substituted with alkyl or halogen, or pyridyl; the boronic acid $R^4B(OH)_2$ where $R^4$ is alkyl or phenyl optionally substituted with alkyl or halogen; the phosphonic acid $R^5PO_3H_2$ where $R^5$ is alkyl, haloalkenyl, or phenyl optionally substituted with alkyl or halogen: the sulfuric acid $R^6OSO_3H$ where $R^6$ is hydrogen or alkyl; or the alkanoic acid $X\text{-}(CH_2)_qCO_2H$ where q is 0 to 11, X is halogen, trihaloalkyl, haloalkenyl, cyano, aminocarbonyl, or $CO_2R^7$ where $R^7$ is hydrogen or alkyl; and wherein further, the following terms whether used alone or as part of a larger moiety refer to the associated number of carbon atoms: (1) "alkyl" or "alkoxy" refers to 1 to 6 carbon atoms, (2) "alkenyl" refers to 2 to 12 carbon atoms; and (3) "cycloalkyl" refers to 3 to 8 carbon atoms.

2. The acid salt of claim 1 where R is alkoxycarbonyl, alkoxycarbonylamino, cycloalkylalkoxy, 2-alkyl-2H-tetrazol-5-yl, or 2-haloalkyl-2H-tetrazol-5-yl;

$R^1$ is trihaloalkyl, or trihaloalkoxy;

n is 0, or 1; and, wherein said salt is derived from D-glucuronic acid, or the sulfonic acid $R^2SO_3H$ where $R^2$ is alkyl, haloalkyl, hydroxyalkyl, D-10-camphoryl, or phenyl optionally substituted with alkyl or halogen.

3. The acid salt of claim 1 where R is 2-ethyl-2H-tetrazol-5-yl; $R^1$ is trifluoromethyl; n is 1; and said salt is derived from the sulfonic acid $R^2SO_3H$ where $R^2$ is alkyl, or hydroxyalkyl.

4. An insecticidal composition comprising an insecticidally effective amount of an acid salt of claim 1, and an insecticidally compatible carrier.

5. An insecticidal composition comprising an insecticidally effective amount of an acid salt of claim 2, and an insecticidally compatible carrier.

6. An insecticidal composition comprising an insecticidally effective amount of an acid salt of claim 3, and an insecticidally compatible carrier.

7. A method of controlling insects, comprising application of an insecticidally effective amount of a composition of claim 4 to a locus where insect control is desired.

8. A method of controlling insects, comprising application of an insecticidally effective amount of a composition of claim 5 to a locus where insect control is desired.

9. A method of controlling insects, comprising application of an insecticidally effective amount of a composition of claim 6 to a locus where insect control is desired.

10. An insecticidal, photostable, agriculturally acceptable salt of an organic or inorganic acid having the formula:

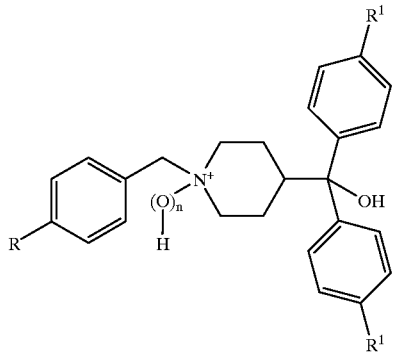

wherein the acid employed to form said salt, and n, q, X, R, $R^1$, $R^2$, $R^3$, $R^4$, $R^5$, $R^6$, and $R^7$ are as set forth in the following table:

| | | | | Photostable N-Benzyl-4-benzhydrol-piperidine Salt Derived From The Sulfonic Acid $R^2SO_3H$ or Other Acid, Wherein: | |
|---|---|---|---|---|---|
| Cmpd. No. is | R is | $R^1$ is | n is | $R^2$ is | Other Acid is |
| 1 | $CO_2CH(CH_3)_2$ | $OCF_3$ | 0 | — | HCl |
| 2 | $CO_2CH(CH_3)_2$ | $OCF_3$ | 0 | $C_2H_5$ | — |
| 3 | 2-methyl-2H-tetrazol-5-yl | $CF_3$ | 0 | — | HCl |
| 4 | 2-methyl-2H-tetrazol-5-yl | $OCF_3$ | 0 | — | HCl |
| 5 | 2-methyl-2H-tetrazol-5-yl | $OCF_3$ | 0 | $C_2H_5$ | — |
| 6 | 2-ethyl-2H-tetrazol-5-yl | $CF_3$ | 0 | — | HCl |
| 7 | 2-ethyl-2H-tetrazol-5-yl | $CF_3$ | 0 | $C_2H_5$ | — |
| 8 | 2-ethyl-2H-tetrazol-5-yl | $OCF_3$ | 0 | — | HCl |
| 9 | 2-ethyl-2H-tetrazol-5-yl | $OCF_3$ | 0 | $C_2H_5$ | — |
| 10 | 2-(2-fluoroethyl-2H-tetrazol-5-yl | $OCF_3$ | 0 | — | HCl |
| 11 | Cyclopropylmethoxy | $CF_3$ | 1 | — | HCl |
| 12 | Cyclopropylmethoxy | $CF_3$ | 1 | $C_2H_5$ | — |
| 13 | Cyclopropylmethoxy | $CF_3$ | 1 | $C_2H_4OH$ | — |
| 15 | Cyclopropylmethoxy | $CF_3$ | 1 | — | D-glucuronic acid |
| 16 | $NHCO_2CH_3$ | $OCF_3$ | 1 | — | HCl |
| 17 | $NHCO_2CH_3$ | $OCF_3$ | 1 | $C_2H_5$ | — |
| 18 | $NHCO_2CH_3$ | $OCF_3$ | 1 | $C_2H_4OH$ | — |
| 20 | $NHCO_2CH_3$ | $OCF_3$ | 1 | — | D-glucuronic acid |
| 21 | $NHCO_2CH(CH_3)_2$ | $CF_3$ | 1 | — | HCl |
| 22 | $NHCO_2CH(CH_3)_2$ | $CF_3$ | 1 | $C_2H_5$ | — |
| 23 | $NHCO_2CH(CH_3)_2$ | $CF_3$ | 1 | $C_2H_4OH$ | — |
| 25 | $NHCO_2CH(CH_3)_2$ | $CF_3$ | 1 | — | D-glucuronic acid |
| 26 | 2-methyl-2H-tetrazol-5-yl | $CF_3$ | 0 | — | HCl |
| 27 | 2-methyl-2H-tetrazol-5-yl | $CF_3$ | 0 | $C_2H_5$ | — |
| 28 | 2-methyl-2H-tetrazol-5-yl | $CF_3$ | 0 | $C_2H_4OH$ | — |
| 30 | 2-methyl-2H-tetrazol-5-yl | $CF_3$ | 1 | — | D-glucuronic acid |
| 31 | 2-ethyl-2H-tetrazol-5-yl | $CF_3$ | 1 | — | HCl |
| 32 | 2-ethyl-2H-tetrazol-5-yl | $CF_3$ | 1 | $CH_3$ | — |
| 33 | 2-ethyl-2H-tetrazol-5-yl | $CF_3$ | 1 | $C_2H_5$ | — |
| 34 | 2-ethyl-2H-tetrazol-5-yl | $CF_3$ | 1 | $C_5H_{11}$ | — |
| 35 | 2-ethyl-2H-tetrazol-5-yl | $CF_3$ | 1 | $C_6H_{11}$ | — |
| 36 | 2-ethyl-2H-tetrazol-5-yl | $CF_3$ | 1 | $CF_3$ | — |
| 37 | 2-ethyl-2H-tetrazol-5-yl | $CF_3$ | 1 | $C_6H_5$ | — |
| 38 | 2-ethyl-2H-tetrazol-5-yl | $CF_3$ | 1 | 4-$(CH_3)C_6H_4$ | — |
| 39 | 2-ethyl-2H-tetrazol-5-yl | $CF_3$ | 1 | 2,4,6-$(CH_3)_3C_6H_2$ | — |
| 40 | 2-ethyl-2H-tetrazol-5-yl | $CF_3$ | 1 | D-10-camphor | — |
| 41 | 2-ethyl-2H-tetrazol-5-yl | $CF_3$ | 1 | $C_2H_4OH$ | — |
| 44 | 2-ethyl-2H-tetrazol-5-yl | $CF_3$ | 1 | — | D-glucuronic acid |
| 45 | 2-ethyl-2H-tetrazol-5-yl | $CF_3$ | 0 | $CH_3$ | — |
| 46 | 2-ethyl-2H-tetrazol-5-yl | $CF_3$ | 0 | — | HBr |
| 47 | 2-ethyl-2H-tetrazol-5-yl | $CF_3$ | 0 | 4-$(CH_3)C_6H_4$ | — |
| 48 | 2-ethyl-2H-tetrazol-5-yl | $CF_3$ | 0 | — | D-glucuronic acid |
| 49 | 2-ethyl-2H-tetrazol-5-yl | $CF_3$ | 0 | $C_2H_4OH$ | — |
| 52 | 2-ethyl-2H-tetrazol-5-yl | $CF_3$ | 1 | 4-$ClC_6H_4$ | — |
| 53 | 2-ethyl-2H-tetrazol-5-yl | $CF_3$ | 1 | — | $H_3BO_3$ |
| 54 | 2-ethyl-2H-tetrazol-5-yl | $CF_3$ | 1 | — | $H_3PO_4$ |
| 55 | 2-ethyl-2H-tetrazol-5-yl | $CF_3$ | 1 | — | maleic acid |
| 56 | 2-ethyl-2H-tetrazol-5-yl | $CF_3$ | 1 | — | fumaric acid |
| 57 | 2-ethyl-2H-tetrazol-5-yl | $CF_3$ | 1 | — | phthalic acid |

| | | | | Photostable N-Benzyl-4-benzhydrol-piperidine Salt Derived From The Carboxilic Acid $R^3CO_2H$, Wherein: |
|---|---|---|---|---|
| Cmpd. No. is | R is | $R^1$ is | n is | $R^3$ is |
| 58 | 2-ethyl-2H-tetrazol-5-yl | $CF_3$ | 1 | H |
| 59 | 2-ethyl-2H-tetrazol-5-yl | $CF_3$ | 1 | $CH_3$ |
| 60 | 2-ethyl-2H-tetrazol-5-yl | $CF_3$ | 1 | $CF_3$ |
| 61 | 2-ethyl-2H-tetrazol-5-yl | $CF_3$ | 1 | CO2H |
| 62 | 2-ethyl-2H-tetrazol-5-yl | $CF_3$ | 1 | 4-Cl-phenyl |
| 63 | 2-ethyl-2H-tetrazol-5-yl | $CF_3$ | 1 | 4-$CH_3$-phenyl |
| 64 | 2-ethyl-2H-tetrazol-5-yl | $CF_3$ | 1 | pyridin-2-yl |
| 65 | 2-ethyl-2H-tetrazol-5-yl | $CF_3$ | 1 | $CH_3$ |
| 66 | 2-ethyl-2H-tetrazol-5-yl | $CF_3$ | 1 | 4-Cl-phenyl |
| 67 | 2-ethyl-2H-tetrazol-5-yl | $CF_3$ | 1 | 4-$CH_3$-phenyl |

-continued

| | | | | Photostable N-Benzyl-4-benzhydrol-piperidine Salt Derived From The Phosphonic Acid $R^5PO_3H_2$, Wherein: |
|---|---|---|---|---|
| Cmpd. No. is | R is | $R^1$ is | n is | $R^5$ is |
| 68 | 2-ethyl-2H-tetrazol-5-yl | $CF_3$ | 1 | $CH_3$ |
| 69 | 2-ethyl-2H-tetrazol-5-yl | $CF_3$ | 1 | 4-Cl-phenyl |
| 70 | 2-ethyl-2H-tetrazol-5-yl | $CF_3$ | 1 | 4-$CH_3$-phenyl |
| 71 | 2-ethyl-2H-tetrazol-5-yl | $CF_3$ | 1 | $CH_2CF{=}CF_2$ |

| | | | | Photostable N-Benzyl-4-benzhydrol-piperidine Salt Derived From The Sulfuric Acid $R^6OSO_3H$, Wherein: |
|---|---|---|---|---|
| Cmpd. No. is | R is | $R^1$ is | n is | $R^6$ is |
| 72 | 2-ethyl-2H-tetrazol-5-yl | $CF_3$ | 1 | H |
| 73 | 2-ethyl-2H-tetrazol-5-yl | $CF_3$ | 1 | $CH_3$ |

| | | | | Photostable N-Benzyl-4-benzhydrol-piperidine Salt Derived From The Alkanoic Acid $X{-}(CH_2)_qCO_2H$, Wherein: | | |
|---|---|---|---|---|---|---|
| Cmpd. No. is | R is | $R^1$ is | n is | q is | X is | $R^7$ is |
| 74 | 2-ethyl-2H-tetrazol-5-yl | $CF_3$ | 1 | 2 | Cl | — |
| 75 | 2-ethyl-2H-tetrazol-5-yl | $CF_3$ | 1 | 2 | $CF_3$ | — |
| 76 | 2-ethyl-2H-tetrazol-5-yl | $CF_3$ | 1 | 1 | $CF{=}CF_2$ | — |
| 77 | 2-ethyl-2H-tetrazol-5-yl | $CF_3$ | 1 | 1 | CN | — |
| 78 | 2-ethyl-2H-tetrazol-5-yl | $CF_3$ | 1 | 2 | $CONH_2$ | — |
| 79 | 2-ethyl-2H-tetrazol-5-yl | $CF_3$ | 1 | 4 | $CO_2R^7$ | H |
| 80 | 2-ethyl-2H-tetrazol-5-yl | $CF_3$ | 1 | 8 | $CO_2R^7$ | $CH_3$; |

and wherein said salt is at least about 2.5 times more photostable than its non-ionic parent.

11. An insecticidal composition comprising an insecticidally effective amount of an acid salt of claim 10, and an insecticidally compatible carrier.

12. A method of controlling insects, comprising application of an insecticidally effective amount of a composition of claim 10 to a locus where insect control is desired.

13. A method for enhancing the photostability of a N-benzyl-4-benzhydrolpiperidine or its corresponding N-oxide, comprising forming said piperidine or N-oxide as an agriculturally acceptable organic or inorganic acid salt, with the proviso that salts formed with salicylic acid, 5-chlorosalicylic acid, or 3,5-dichlorosalicylic acid are excluded.

14. The method of claim 13, wherein said piperidine or N-oxide thereof have the formula

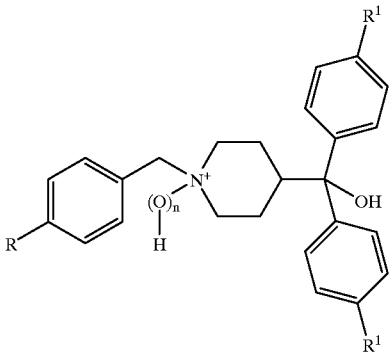

where R is alkoxycarbonyl, alkoxycarbonylamino, cycloalkylalkoxy, 2-alkyl-2H-tetrazol-5-yl, or 2-haloalkyl-2H-tetrazol-5-yl; $R^1$ is trihaloalkyl, or trihaloalkoxy; and n is 0, or 1.

15. The method of claim 14, wherein R is 2-ethyl-2H-tetrazol-5-yl; $R^1$ is trifluoromethyl; and n is 1.

16. The method of claim 13, wherein said salt is derived from hydrochloric acid, hydrobromic acid, boric acid, phosphoric acid, maleic acid, fumaric acid, phthalic acid, D-glucuronic acid; the sulfonic acid $R^2SO_3H$ where $R^2$ is alkyl, haloalkyl, hydroxyalkyl, D-10-camphoryl, or phenyl optionally substituted with alkyl or halogen; the carboxylic acid $R^3CO_2H$ where $R^3$ is hydrogen, alkyl, trihaloalkyl, carboxyl, phenyl optionally substituted with alkyl or halogen, or pyridyl; the boronic acid $R^4B(OH)_2$ where $R^4$ is alkyl or phenyl optionally substituted with alkyl or halogen; the phosphonic acid $R^5PO_3H_2$ where $R^5$ is alkyl, haloalkenyl, or phenyl optionally substituted with alkyl or halogen: the sulfuric acid $R^6OSO_3H$ where $R^6$ is hydrogen or alkyl; or the alkanoic acid $X\text{-}(CH_2)_qCO_2H$ where q is 0 to 11, X is halogen, trihaloalkyl, haloalkenyl, cyano, aminocarbonyl, or $CO_2R^7$ where $R^7$ is hydrogen or alkyl.

17. The method of claim 16, wherein said salt is derived from hydrochloric acid, D-glucuronic acid, or the sulfonic acid wherein $R^2$ is alkyl, haloalkyl, hydroxyalkyl, D-10-camphoryl, or phenyl optionally substituted with alkyl or halogen.

18. The method of claim 13, wherein R is 2-ethyl-2H-tetrazol-5-yl; $R^1$ is trifluoromethyl; n is 1; and said salts are derived from hydrochloric acid, D-glucuronic acid, or the sulfonic acid wherein $R^2$ is alkyl or hydroxyalkyl.

* * * * *